United States Patent [19]

Klein

[11] Patent Number: 5,762,631

[45] Date of Patent: Jun. 9, 1998

[54] METHOD AND SYSTEM FOR REDUCED FRICTION INTRODUCTION OF COAXIAL CATHETERS

[75] Inventor: Enrique J. Klein, Los Altos, Calif.

[73] Assignee: Localmed, Inc., Palo Alto, Calif.

[21] Appl. No.: 502,693

[22] Filed: Jul. 14, 1995

[51] Int. Cl.[6] .................... A61M 5/00; B29C 63/00
[52] U.S. Cl. .................. 604/171; 604/264; 604/280; 264/171.12; 264/172.1
[58] Field of Search ............... 604/264, 280, 604/282, 171, 96, 101, 104; 264/171.12, 172.1, 173, 209.4, 284, 150; 606/192, 194, 108

[56] References Cited

U.S. PATENT DOCUMENTS

| 1,596,754 | 8/1926 | Moschelle . | |
|---|---|---|---|
| 3,872,893 | 3/1975 | Roberts | 264/172.1 |
| 4,410,476 | 10/1983 | Redding et al. | 264/172.1 |
| 4,421,810 | 12/1983 | Rasmussen | 264/172.1 |
| 4,681,570 | 7/1987 | Dalton | 604/282 |
| 4,689,174 | 8/1987 | Lupke | 264/172.1 |
| 4,900,314 | 2/1990 | Quackenbush | 604/282 |
| 5,054,501 | 10/1991 | Chuttani et al. | 128/772 |
| 5,122,125 | 6/1992 | Deuss | 604/282 |
| 5,147,317 | 9/1992 | Shank et al. | 604/164 |
| 5,217,440 | 6/1993 | Frassica | 604/282 |
| 5,244,619 | 9/1993 | Burnham | 264/173 |
| 5,337,733 | 8/1994 | Bauerfeind et al. | 604/282 |
| 5,404,887 | 4/1995 | Prather | 128/772 |
| 5,417,208 | 5/1995 | Winkler | 604/280 |
| 5,445,624 | 8/1995 | Jimenez | 604/280 |
| 5,496,292 | 3/1996 | Burnham | 604/282 |
| 5,571,086 | 11/1996 | Kaplan et al. | 604/96 |

FOREIGN PATENT DOCUMENTS

WO 92/19308  11/1992  WIPO .
WO 93/23105  11/1993  WIPO .

OTHER PUBLICATIONS

Product Brochure–Trio 14 "Re–engineering Over–the–Wire Balloon Technology, " Scimed®. © 1994 Scimed Life Systems.

Primary Examiner—Robert A. Clarke
Assistant Examiner—David J. Cho
Attorney, Agent, or Firm—Townsend And Townsend And Crew LLP

[57] ABSTRACT

Catheter systems comprising a base catheter and a sleeve catheter are modified to have reduced sliding friction therebetween. The sleeve catheter is received over the base catheter, and an inner luminal surface of the sleeve catheter or outer surface of the base catheter is modified to have surface irregularities to reduce sliding friction. Preferably, the surface irregularities are circumferentially spaced-apart V-spaced peaks. Such peaks may be formed by fabricating tubular catheter bodies in an extrusion tool having a mold or die with correspondingly shaped V-shaped grooves therein. Alternatively, the surface irregularities may be imparted using a mold or mandrel which is placed over or in a tubular catheter body, where the desired geometry is transferred by heating the catheter.

13 Claims, 4 Drawing Sheets

2

METHOD AND SYSTEM FOR REDUCED FRICTION INTRODUCTION OF COAXIAL CATHETERS

BACKGROUND OF THE INVENTION

1. Field of the Invention

The present invention relates generally to methods and devices for performing multiple, sequential intraluminal procedures. In particular, the present invention is related to a method and catheter system for reducing friction between coaxial catheters when they are axially translated relative to each other during the performance of such methods using such systems.

Intravascular and other intraluminal procedures frequently require the sequential introduction of two or more coaxial catheters, where each catheter provides a particular function or treatment modality which must be delivered to a common treatment location. For example, it has been proposed to treat atherosclerosis using two or more sequential procedures intended to address different parts of the overall therapy. Initial treatment often comprises angioplasty or atherectomy using a particular type of catheter followed by drug delivery, stent placement, perfusion, imaging, or the like, in order to further treat or assess the target location. Of particular interest to the present invention, systems and methods employing a base catheter for effecting the primary treatment and a sleeve catheter for effecting the secondary treatment or imaging have been proposed in copending application Ser. No. 08/222,143, assigned to the assignee of the present application, the full disclosure of which is incorporated herein by reference. Using such methods in coronary applications, the base catheter and sleeve catheter will usually be introduced together through a guiding catheter which extends from a primary percutaneous access site, such as a femoral access site in the groin, to a coronary ostium. The base catheter and sleeve catheter can be introduced through the guiding catheter to the target location within the coronary vasculature, and the two catheters then translated axially relative to each other to selectively or simultaneously position the working end of each catheter at the target location.

While a significant improvement over the use of separate catheters for each intended treatment or diagnostic protocol, such coaxial catheter systems suffer from the limited availability of lumen area in the guiding catheter. Because of the limited lumen area, the catheters must be made to be close fitting, with the sleeve catheter usually having a diameter which is no more than 10% to 25% greater than the outer diameter of the base catheter. Under such circumstances, friction between the inner lumenal surface of the sleeve catheter and the outer surface of the base catheter can be significant, rendering it difficult to axially position the catheters relative to one another after they have been deployed in the vasculature. Additionally, since the combination of sleeve catheter and base catheter will usually present a larger combined profile than a single-purpose catheter, there may be greater friction between the outer surface of the sleeve catheter and the inner surface of the guiding catheter during the initial introduction.

For these reasons, it would be desirable to provide improved methods for the intraluminal introduction of coaxial catheter systems where the friction between such catheters is reduced. If would be further desirable if the friction between the combined coaxial catheters and a third coaxial catheter, such as a coronary guiding catheter, is also reduced. It would be still further desirable to provide methods for fabricating tubular catheters having reduced surface friction when employed with coaxial catheters which are disposed either over or within a lumen of the tubular catheter. It would be still further desirable to provide a catheter system having a base catheter and a sleeve catheter, where the friction between the base catheter and the sleeve catheter is reduced to lower the force necessary to slide the catheters relative to each other.

2. Description of the Background Art

A guide wire having an extruded sleeve with an unsmooth surface is described in U.S. Pat. No. 5,404,887. An angioplasty catheter which may incorporate the design of U.S. Pat. No. 5,404,887 is sold by SciMed Life Systems, Inc., Minneapolis, Minn., under the trade name TRIO 14. A guiding catheter having channels on its interior surface resulting from inclusion of a spiraled reinforcement layer is shown in WO 93/23105. A catheter having an irregular outer or inner surface resulting from an embedded reinforcing member is described in WO 92/19308. Other catheter structures having projections or features on their interior and/or exterior surfaces are described in U.S. Pat. Nos. 5,217,440; 5,122,125; 5,054,501; and 1,596,754.

The construction and use of sleeve catheters for a variety of purposes are described in U.S. Pat. No. 5,336,178, and copending application Ser. Nos. 08/047,737; 08/222,143; 08/461,222 (FWC of 08/221,613); 08/305,250; and 08/401,541.

SUMMARY OF THE INVENTION

The method of the present invention for introducing a sleeve catheter over a base catheter comprises introducing a base catheter over a guide wire to a target location within a body lumen, usually a blood vessel, and more usually a coronary artery. The sleeve catheter is introduced coaxially over the base catheter to the target location, sometimes being pre-loaded and sometimes being post-loaded over the base catheters, and then being introduced simultaneously with the base catheter. At least one of the exterior surface of the base catheter and the interior surface of the sleeve catheter has an irregular surface which reduces friction between the sleeve catheter and the base catheter as they are axially translated relative to each other. Alternatively, both the exterior surface of the base catheter and the interior surface of the sleeve catheter will have irregular surfaces. Optionally, the base catheter and the sleeve catheter may be introduced through a guiding catheter, where the exterior surface of the sleeve catheter has an irregular surface in order to reduce sliding friction between the sleeve catheter and the guiding catheter. A preferred irregular surface is characterized by a continuous, circumferential pattern of V-shaped peaks, where the peaks are preferably circumferentially spaced-apart by an arc in the range from 6° to 24°. Such V-shaped peaks may be aligned axially (i.e., in a direction parallel to the axial direction of the catheter), as a spiral over the catheter, or in a zig-zag pattern over the catheter surface.

The present invention also provides a method for fabricating a tubular catheter having an irregular surface intended to reduce sliding friction when used with a coaxial catheter. The method comprises extruding a polymeric resin through an extrusion tool comprising an outer die and an inner pin. At least one of the die and pin is patterned to produce a repeatable pattern of surface irregularity as the tubular catheter is extruded through the tool. Optionally, both the pin and the die may be patterned to produce a tubular catheter having surface irregularities on both its inner (lumenal) and outer surfaces. Preferably, the die or pin irregularities will comprise a continuous, circumferential pattern of V-shaped grooves which will impart a pattern of V-shaped peaks on the catheter surface as the extruded catheter material is drawn through the tool. While the arc between circumferentially spaced-apart grooves remains generally unchanged in the extrusion draw-down process that forms the peaks on the catheter surface, the die groove depth generally corresponds to a substantially diminished peak height in the extrusion since the radial features in the tool are drawn down pronouncedly during the extrusion process. Typically, a tool groove in the range from 0.1 mm to 1.0 mm can provide an extruded peak height in the range from 0.01 mm to 0.05 mm. The tubular catheter may be drawn without rotation through the extrusion tool which produces a pattern of linear, axially-aligned peaks on the catheter surface. Alternatively, the tubular catheter may be rotated continuously or intermittently as it is drawn through the extrusion tool, thus producing a spiral, zig-zag, serpentine, or other pattern of peaks on the catheter surface.

The present invention provides a second method for fabricating a tubular catheter having an irregular surface. In this method, a tubular catheter is first extruded, either in a conventional manner or in the manner just described for producing generally axially-aligned peaks on a catheter surface. Additional surface irregularities may be formed (or the initial surface irregularities maintained) by imprinting such irregularities onto a surface of the catheter after the extruding step. In particular, surface irregularities may be imprinted over the inner (lumenal) surface of the tubular catheter by positioning the extruded catheter body over a mandrel having a preselected pattern of surface irregularities (usually grooves or other cavities) and heating at least a portion of the catheter body to imprint the pattern from the mandrel onto the inner surface of the catheter. In order to form surface irregularities on the exterior surface of the catheter, the extruded catheter body is positioned in a mold having a preselected pattern of surface irregularities (again, typically grooves or other cavities), solid mandrel(s) are positioned in the lumen(s) of the catheter for support, and heating at least a portion of the catheter body to imprint the pattern from the mold onto the outer surface of the catheter.

The catheter system according to the present invention comprises a base catheter and a sleeve catheter. The base catheter has a proximal end, a distal end, and an interactive device near the distal end. The sleeve catheter has a proximal end, a distal end, an axial lumen, and an interactive device near the distal end. The axial lumen of the sleeve catheter receives the base catheter, in the manner generally described above, and at least the lumenal surface of the sleeve catheter includes surface irregularities to reduce surface friction between the base catheter and the sleeve catheter. Preferably, the surface irregularities comprise a plurality of V-shaped peaks, where the peaks are circumferentially spaced-apart by an arc in the range from 6° to 24°, and the peaks may be aligned axially, spirally, in a serpentine pattern, or in a zig-zag pattern.

The present invention still further provides sleeve catheters which are produced by the fabrication methods described above.

DESCRIPTION OF THE SPECIFIC EMBODIMENTS

Figure 1:
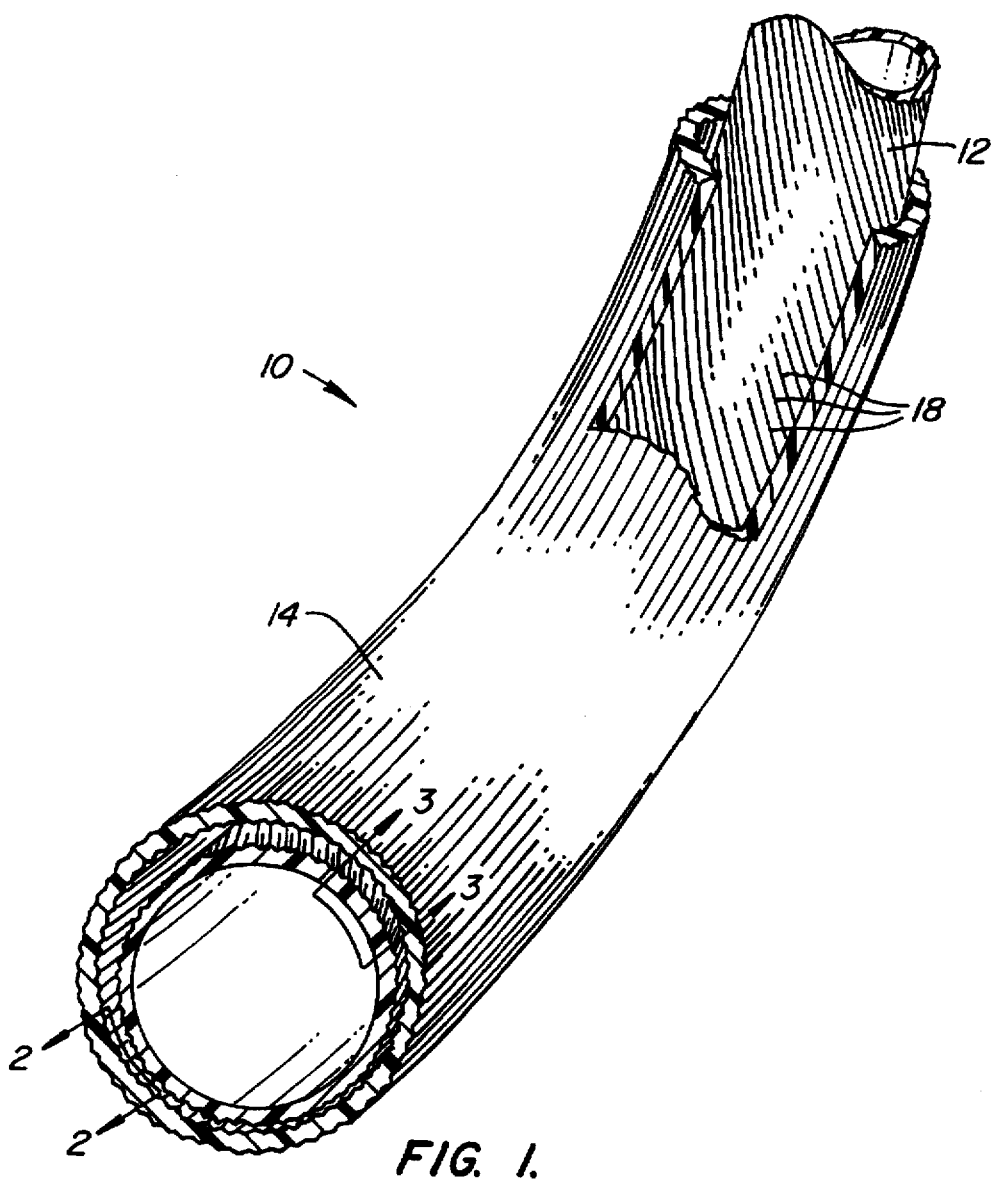
FIG. 1 is a perspective view of a portion of a catheter system constructed in accordance with the principles of the present invention and including an inner base catheter having an exterior grooved surface and an outer sleeve catheter having an exterior and an interior grooved surface.

The present invention provides methods and devices for performing multiple, sequential intraluminal procedures on a patient as part of therapeutic or diagnostic treatment. By "intraluminal," it is meant that the procedures occur at a target location within a body lumen, usually being within the patient vasculature, more usually being within the arterial system, including the coronary arteries, the peripheral arteries, and the cerebral arteries. The methods and devices of the present invention, however, are not limited to use in the vascular system, and may also be advantageously employed in other body structures, including the prostate via the prostatic urethra, (e.g. to treat benign prostatic hypertrophy, prostatitis, and adenocarcinoma), the fallopian tubes via their lumens (to treat strictures), brain parenchyma (to treat Parkinson's disease), and the like.

The "target location" within the body lumen will usually be diseased or be suspected of being diseased. In the case of vascular treatment, the target locations will usually be stenotic regions where blood flow is restricted as a result of atheroma deposits or plaque. Diseased sites within other body lumens are well-known and described in the medical literature.

By "multiple" procedures, it is meant that at least two interventional and/or diagnostic, procedures will be performed as part of a single treatment regimen. Interventional procedures may also be referred to as therapeutic and include revascularization techniques, such as balloon angioplasty, laser angioplasty, ultrasonic angioplasty, atherectomy, and the like; drug delivery techniques; stent placement techniques; axial scoring or slitting of plaque prior to dilatation by balloon angioplasty; and the like. Diagnostic procedures include imaging particularly ultrasonic imaging but also including angioscopy, contrast delivery, and the like. By "sequential," it is meant that one procedure will be performed followed by performing another without having to exchange catheters over a guidewire, usually in any order, with or without repetitions. In the preferred case of intravascular treatment, at least one of the procedures will usually be therapeutic, more usually being balloon, laser or ultrasonic angioplasty, or atherectomy, while the other procedure may be therapeutic or diagnostic usually being drug delivery, perfusion, stent placement, pre-slitting of the plaque prior to angioplasty or imaging.

The methods of the present invention will utilize both a base catheter and a sleeve catheter which is slidably received over the base catheter. Each of the base and sleeve catheters will include an interactive device at or near its distal end, and the catheters will usually be introduced together with the sleeve catheter being disposed over the base catheter. Once the distal ends of the catheters reach a location near the treatment site, the catheters may be axially translated relative to each other in order to sequentially or simultaneously position each interactive device at the treatment site. Conveniently, the base catheter can be a conventional therapeutic or diagnostic catheter usually being a therapeutic catheter more usually being an angioplasty catheter or an atherectomy catheter.

The sleeve catheter is sized to be received over the base catheter and provided with an interactive capability selected to complement or enhance the therapeutic capability of the base catheter. For example, it will frequently be advantageous to provide an imaging sleeve catheter with either an angioplasty or atherectomy base catheter, where the imaging capability can help assess the stenotic region prior and post treatment in order to provide more effective treatment. Drug delivery sleeve catheters are particularly useful to treat a target location after an angioplasty procedure in order to inhibit abrupt closure and restenosis. Perfusion sleeve catheters are ideally suited to provide blood flow distal to the target location when used in conjunction with conventional angioplasty balloon catheters during prolonged balloon inflation. Radially expandable sleeve catheters also permit carrying and subsequent placement of stents and grafts in combination with balloon angioplasty catheters. Alternatively, radially expandable sleeve catheters may carry cutting blades or other elements which may be deployed to score arterial plaque prior to balloon angioplasty.

The lumen of the sleeve catheter which receives the base catheter need not extend the entire length of the base catheter. Instead, a proximal portion of the sleeve catheter can consist essentially of a small diameter rod or tube, with an outside diameter typically in the range from 0.3 mm to 0.8 mm, which has sufficient flexibility to be introduced through the guiding catheter and the relatively non-tortuous regions of the vasculature but which has sufficient column strength to facilitate the axial translation of the sleeve catheter distal portion. For example, stainless steel hypotube can be used, where the lumen of the hypotube provides for fluid agent access in the case of a drug delivery device. The remaining description will be directed at embodiments where the sleeve body extends the entire length of the associated base catheter. It will be appreciated, however, that in at least some cases, a rod or narrow diameter tube can be substituted for the larger diameter tube body.

The design and construction of particular interactive devices is well-known and amply described in the patent and medical literature. For example, angioplasty devices and angioplasty catheters which may be used in the present invention are described in U.S. Pat. Nos. 5,041,089; 4,762,129; 4,775,371; 4,323,071, and 4,292,974, the full disclosures of which are incorporated herein by reference. Suitable atherectomy devices and catheters are described in U.S. Pat. Nos. 4,979,951; 5,071,425; Re. 33,569; 4,781,186; 4,926,858; 5,047,040; 5,181,920; 5,084,010; 5,226,909; 5,092,873; 5,222,966; 5,242,460; and 5,250,059, the full disclosures of which are incorporated herein by reference. Interventional laser angioplasty systems are commercially available from suppliers such as Trimedyne, Inc., Tustin, Calif., under the tradenames OPTILASE™, CARDIOLASE™ and LASERPROBE™. Interventional cardiovascular ultrasound systems for the destruction of plaque are described in U.S. Pat. Nos. 3,565,062 and 4,692,139, and WO 93/21835, the full disclosures of which are incorporated herein by reference, and Siegel et al. (1990) J. Am. Col. Cardiol. 15:345-351. Imaging devices suitable for use as the interactive device of the present invention will usually be ultrasonic, phased-array devices, such as described in U.S. Pat. Nos. 4,841,977 and 4,917,097, the full disclosures of which are incorporated herein by reference. Intravascular stents and stent delivery catheters are described in U.S. Pat. Nos. 4,776,337 and 5,092,877, the full disclosures of which are incorporated herein by reference.

According to the present invention, at least one of the sleeve catheter and the base catheter will have a surface modified to reduce friction between the base catheter and sleeve catheter when they are coaxially translated relative to each other. Optionally, the outer surface of the sleeve catheter may also have a modified surface in order to reduce friction when the sleeve catheter and base catheter are introduced through a guiding catheter. Thus, at least one of the outer surface of the base catheter and the inner surface of the sleeve catheter will be surface modified, and optionally the outer surface of the sleeve catheter will be further modified to reduce friction within the guiding catheter.

Surface modification according to the present invention comprises forming irregularities in the catheter wall so that contact area between the catheter wall and a second contact surface will be limited, thus reducing sliding friction. Such surface irregularities can take a variety of forms, including peaks, ridges, beads, pyramid patterns, waffle patterns, and other protrusions which limit contact area without interfering with free sliding of the coaxial catheters. Preferably, the irregularities will comprise a plurality of circumferentially spaced-apart peaks which extend longitudinally over at least a portion of the catheter body or bodies. Usually, the peaks will be axially aligned with each other, but they may also be arranged in spiral, serpentine, zig-zag, and other regular and irregular patterns. It will often be desirable to provide differing groove patterns on the inner surface of a sleeve catheter and outer surface of a base catheter, when the sleeve catheter and the base catheter are being used together in a catheter system. It will be appreciated that peak patterns having similar dimensions and mating geometries might have a tendency to lock with each other and prevent free relative axial translation of the catheters. Thus, by providing catheters with different surfaces (such as an axially-aligned peak pattern on one of the catheters and a spiral peak pattern on the other), contact area can be greatly minimized without the likelihood of locking between the groove patterns.

The preferred V-shaped peak pattern will comprise peaks which are circumferentially spaced apart by an arc in the range from 6° to 24°, preferably from 10° to 20°, and which have a peak height in the range from 0.01 mm to 0.05 mm, preferably from 0.015 mm to 0.02 mm. Specific methods for forming the peak patterns in the sleeve and base catheters are described hereinafter.

In a first preferred method for forming surface irregularities in the tubular catheter body, a polymeric resin is extruded through an extrusion tool comprising a die and a pin. At least one of the die and pin include a plurality of circumferentially spaced-apart V-shaped grooves which form the V-shaped peaks when the tubular body is extruded through the extrusion tool. It has been found that the V-grooves on the extrusion tool may be sized substantially greater than the desired dimensions of the V-shaped peaks on the catheter surface. Such surface features draw down more rapidly than the diameter or other major geometric features of the catheter body. Typically, it has been found that when the major geometric features in the extrusion tool are sized typically four times greater than the desired dimensions of the catheter, the radial dimensions of the V-shaped grooves or other surface features in the extrusion tool must be sized from ten to twenty times greater than the desired radial dimension of the surface feature on the catheter, usually from twelve to eighteen times greater. Thus, for the exemplary major feature draw down ratio of four to one, for the V-shaped grooves, the groove depth on the tool will typically be in the range from 0.15 mm to 0.3 mm to produce a V-shaped peak on the catheter surface having a height of 0.015 mm.

Extrusion of the tubular catheters of the present invention will be formed in the generally conventional manner, except for the provision of the surface irregularities as described above. Thus, a polymeric resin will be provided and heated above its melting point prior to extrusion through the extrusion tool. Suitable polymeric resins include both natural and synthetic polymers, such as silicone rubber polyethylene, polyvinylchloride, polyurethanes, polyesters, polytetrafluoroethylenes (PTFEs), nylon, and the like. Optionally, the catheter sleeve body may be formed or co-extruded as a composite having one or more reinforcement layers incorporated within the polymeric body in order to enhance its strength, flexibility, pushability, and resistance to kinking. Additionally, the composition of the catheter body may vary along its length, with discrete portions of its length being composed from different materials and/or composites. Typically, the catheter body will be formed using extrusion techniques which are well described in the patent and medical literature.

As an alternative or an addition to formation of the surface features using specially shaped extrusion tools, as described above, surface features may be formed after extrusion process using suitable mandrels, molds, and the like. For example, surface features, such as axial peaks, may be formed over the interior luminal surface of the tubular catheter using a mandrel having axial grooves or other voids formed in its surface. The mandrel may be placed in the lumen, and the tubular catheter body thereafter heated and compressed in order to melt the surface so that material flows into the grooves or voids of the mandrel. In this way, the surface features defined by the mandrel may be imparted to the luminal surface of the tubular catheter. Similarly, external surface features can be imparted to the tubular catheter using a mold having axial grooves or other voids formed in its interior surface. When using a mold, it will often be desirable to support the lumens of the catheter body with solid mandrels. The mold, catheter, or both will be heated in order to at least partially melt the catheter body and form the desired features. Often, the tubular catheter will be formed using the extrusion process described above where features are formed by an extrusion tool having specialized geometry, where such surface features are maintained using specialized molds or mandrels as just described, following the loss of these surface features due to secondary processing, such as tipping, or the like.

Figure 2:
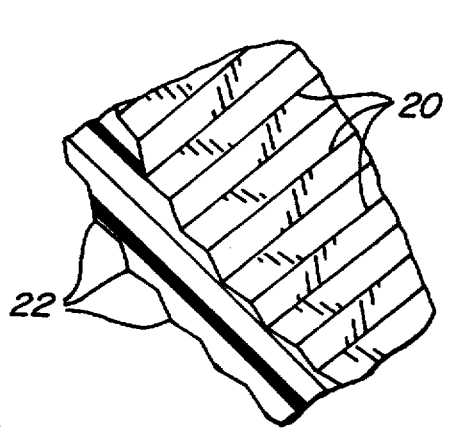
FIG. 2 is a detailed view of a section of the outer sleeve catheter taken along line 2—2 of FIG. 1.
Figure 3:
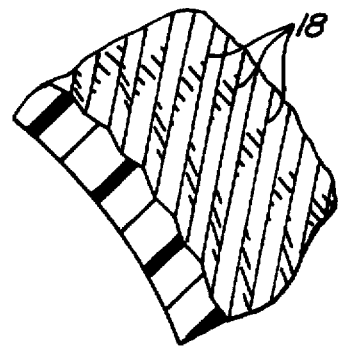
FIG. 3 is a detailed view of the inner base catheter taken along line 3—3 of FIG. 1.

Referring now to FIGS. 1-3, exemplary catheter system 10 comprising a base catheter 12 and a sleeve catheter 14 is illustrated. Base catheter 12 has a plurality of spiral peaks 18 formed over its outer surface, as best illustrated in FIG. 3. The inner surface of the base catheter 18 is smooth, but could optionally employ surface grooves or other irregularities.

The sleeve catheter 14 comprises a plurality of circumferentially spaced-apart peaks 20 over its inner luminal surface and 22 over its outer surface. By employing spiral peaks 18 on the base catheter 12 and axial peaks 20 on the sleeve catheter 14, the likelihood that the peaks of one will seize against the grooves between the peaks of the other is greatly diminished. Moreover, the total contact area between points of the catheters is greatly reduced to that of the crossing points of the contacting peaks, significantly diminishing the sliding friction therebetween. Even if the outer surface of the base catheter 12 were smooth, peaks 20 on the lumen of the sleeve catheter 14 would provide significantly reduced sliding friction therebetween when compared to the sliding friction between two smooth surfaces. By providing axial peaks 22 on the outer surface of the sleeve catheter 14, the combination of base catheter 12 and sleeve catheter 14 may be introduced through a conventional guiding catheter with reduced sliding friction.

Figure 3A:
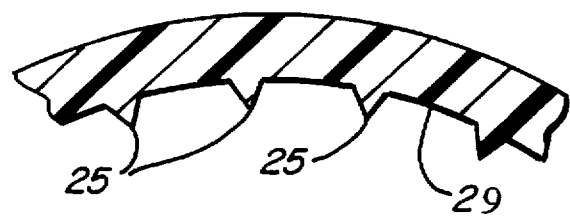
FIGS. 3A and 3B show alternative low friction surfaces according to the present invention.
Figure 3B:
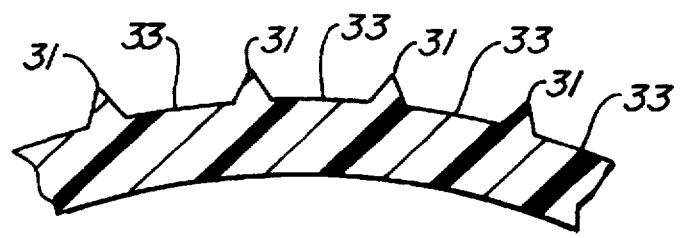

Alternative configurations of low friction surface of the present invention are shown in FIGS. 3A and 3B. FIG. 3A shows peaks 25 circumferentially spaced-apart by a flat region 27 by flat regions 29 on an inner surface of a tubular member. Similarly, FIG. 3B shows peaks 31 spaced-apart by flat regions 33 on an outer surface of a tubular member. The peaks 25 and 31 could be formed into linear, spiral, serpentine, or any other pattern as discussed above.

Figure 4:
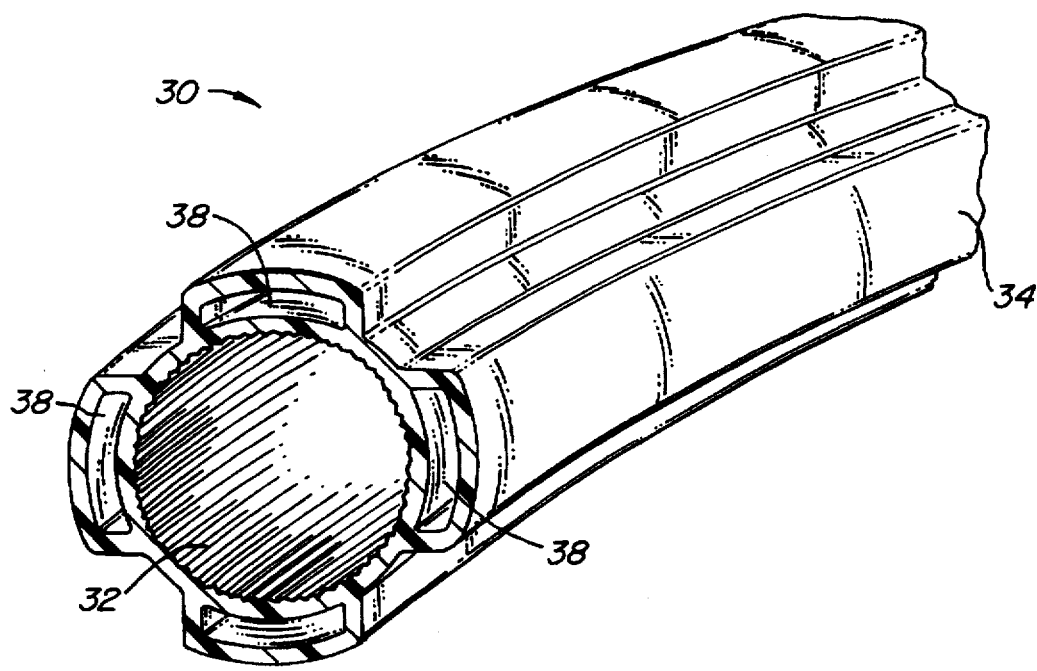
FIG. 4 is a perspective view of a drug delivery sleeve catheter constructed in accordance with the principles of the present invention.

Referring now to FIG. 4, drug delivery catheter 30 having an inner luminal surface 32 modified in accordance with the principles of the present invention will be described. Drug delivery catheter 30 is of the type described in copending application Ser. No. 08/241,428, the full disclosure of which is incorporated herein by reference. Four drug infusion tubes 34, are formed over the exterior surface of the catheter 30. A liquid medium carrying a desired therapeutic agent may be delivered through perfusion lumens 38 of each infusion tube 34. The V-shaped peaks formed over the inner luminal surface will reduce surface friction as the drug infusion catheter 30 is introduced over a conventional balloon catheter, as described in more detail below in connection with FIGS. 6A–6D.

Figure 5:
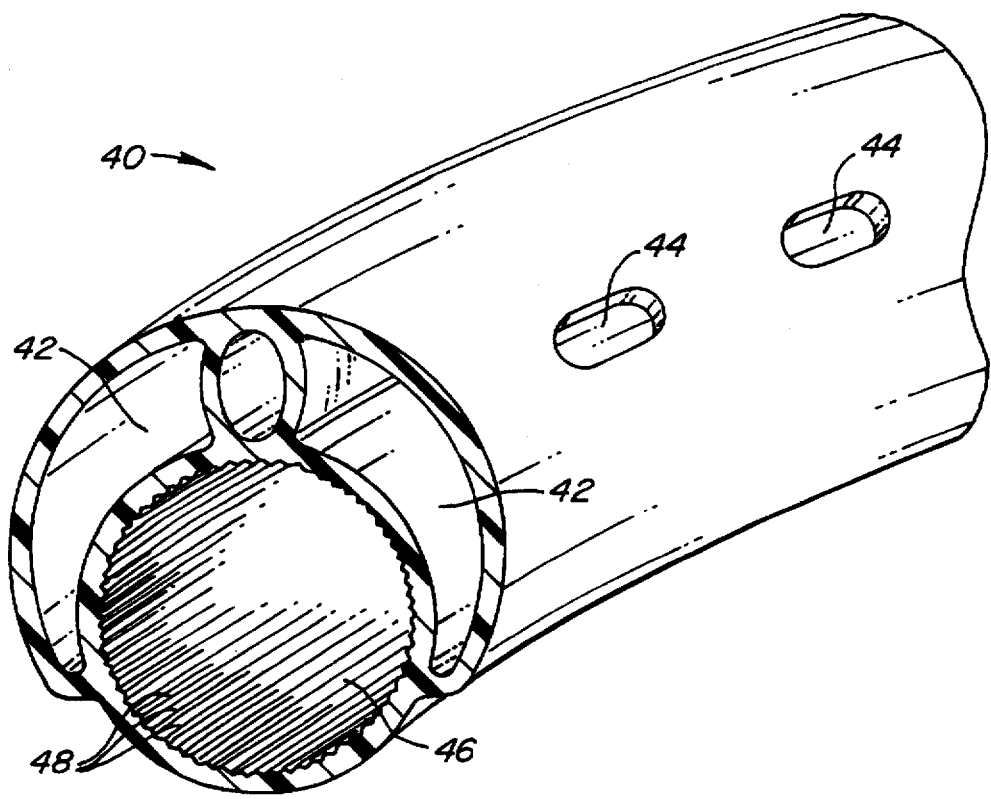
FIG. 5 is a perspective view of a portion of a perfusion flow sleeve catheter constructed in accordance with the principles of the present invention.

A blood perfusion catheter 40 is illustrated in FIG. 5. Catheter 40 includes a pair of perfusion lumens 42 having perfusion ports 44 formed in the wall thereof. Catheter 40 may be disposed over a balloon or other catheter in order to provide for blood perfusion through the lumens 42. A central lumen 46 is provided for receiving the balloon or other catheter, which lumen 46 includes the V-shaped peaks 48 of the present invention. Construction of such perfusion catheters (without surface irregularities formed on the catheter-receiving lumen thereof) is described in copending application Ser. No. 08/461,222 (FWC of 08/221,613), the full disclosure of which is incorporated herein by reference.

Figure 6A:
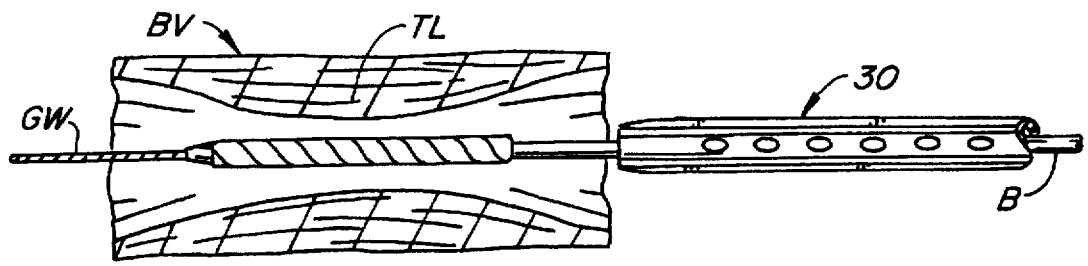
FIGS. 6A–6D illustrate the method of catheter positioning of the present invention employing the drug infusion catheter of FIG. 4 deployed over a conventional angioplasty balloon catheter.
Figure 6B:
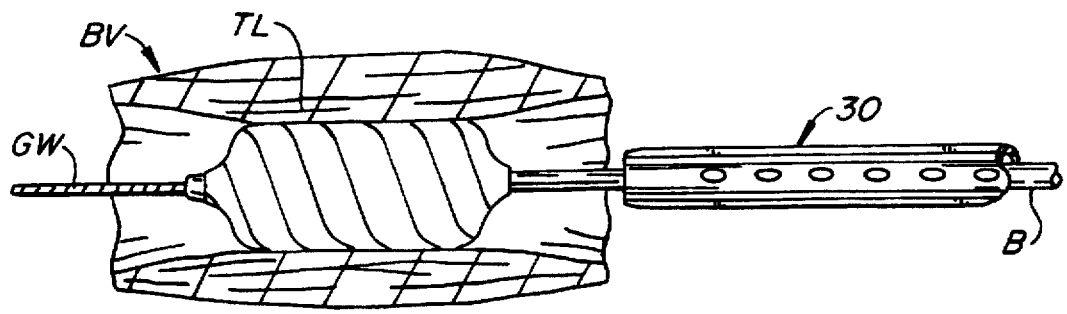

Referring now to FIGS. 6A–6D, a drug infusion catheter 30 may be positioned over a balloon catheter B and introduced to a target location TL in a blood vessel BV over a guide wire GW in a generally conventional manner. After the balloon catheter B is positioned at the target location, as shown in FIG. 6A, the balloon will be inflated to dilate the target location, as shown in FIG. 6B. The drug delivery catheter 30 will remain proximal to the balloon during the balloon inflation.

Figure 6C:
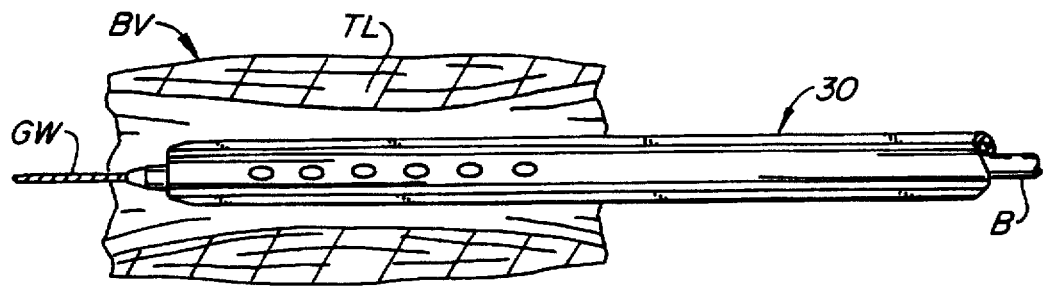
Figure 6D:
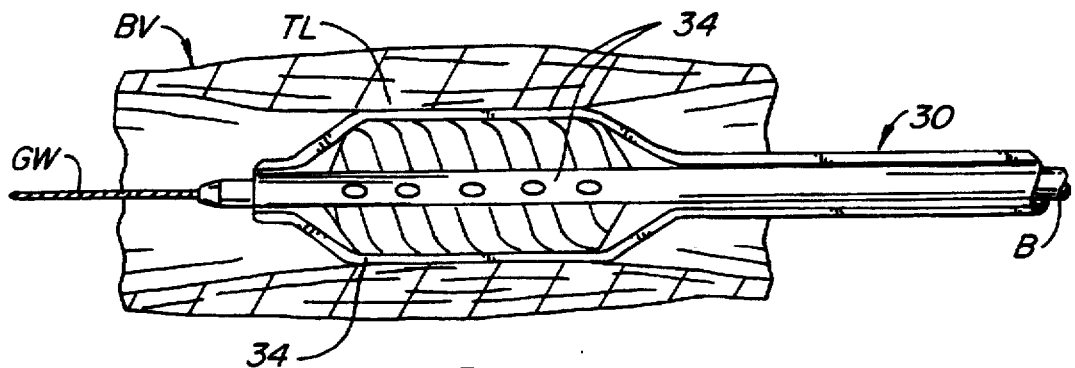

After achieving the desired dilatation, the balloon is deflated, and the drug infusion catheter advanced distally, as shown in FIG. 6C. The low friction surface of the inner lumen of the drug delivery catheter 30 facilitates such distal advancement and allows precise positioning of the catheter 30 over the balloon.

After positioning has been achieved, the balloon of balloon catheter B is again inflated, engaging drug infusion tubes 34 of the drug delivery catheter 30 against the wall of the blood vessel BV. The drug may then be delivered directly into the blood vessel wall through the drug infusion tubes 34.

Although the foregoing invention has been described in some detail by way of illustration and example, for purposes of clarity of understanding, it will be obvious that certain changes and modifications may be practiced within the scope of the appended claims.

What is claimed is:

1. A method for introducing a sleeve catheter over a base catheter into a body lumen, said method comprising:

introducing the base catheter over a guide wire to a target location within the body lumen, and translating the sleeve catheter coaxially over the base catheter while said base catheter is positioned within the body lumen, wherein the base catheter and the sleeve catheter are introduced coaxially through a guiding catheter;

wherein at least a distal portion of the exterior surface of the base catheter and a distal portion of the interior surface of the sleeve catheter have irregular surfaces to reduce friction and wherein the pattern of surface irregularities on the base catheter is selected so that it will not mate with the pattern of surface irregularities on the sleeve catheter.

2. The method as in claim 1, wherein one of the patterns comprises spiral peaks and the other comprises axial peaks.

3. The method as in claim 1, wherein an exterior surface of the sleeve catheter has an irregular surface to reduce sliding friction with the guiding catheter.

4. The method as in claim 1, wherein the irregular surface is characterized by a continuous circumferential pattern of V-shaped peaks.

5. The method as in claim 4, wherein the V-shaped peaks are circumferentially spaced-apart by an arc in the range from 6° to 24°.

6. The method as in claim 5, wherein the V-shaped peaks are aligned in a pattern selected from the group consisting of axial, spiral, and zig-zag.

7. A method for fabricating a tubular catheter having an irregular surface, said method comprising extruding a polymeric resin through an extrusion tool comprising an outer die and an inner pin, wherein at least one of the die and the pin is patterned to produce a repeatable pattern of surface irregularities as the tubular catheter is extruded through said tool, wherein said surface irregularities reduce sliding friction between said tubular catheter and another catheter which is introduced over or through said tubular catheter and which engages the surface with said surface irregularities.

8. The method as in claim 7, wherein both the pin and die are patterned to produce a tubular catheter having inner and outer surfaces with surface irregularities on said inner and outer surfaces.

9. The method as in claim 7, wherein a surface of the die or pin comprises a continuous circumferential pattern of V-shaped grooves which will impart a pattern of V-shaped peaks on the outer or inner surface of the catheter, respectively.

10. The method as in claim 9, wherein the grooves are circumferentially spaced-apart by an arc in the range from 6° to 24°.

11. The method as in claim 10, wherein the grooves have a depth in the range from about 0.1 mm to 1 mm which will impart a drawn down peak height in the range from 0.01 mm to 0.05 mm.

12. The method as in claim 9, wherein the tubular catheter is drawn without rotation through the extrusion tool to produce linear peaks on the catheter.

13. The method as in claim 9, wherein the tubular catheter is rotated as the tubular catheter is drawn through the extrusion tool to produce a spiral or zig-zag peak pattern on the catheter surface.

* * * * *